United States Patent
Perez (10) Patent No.: US 10,471,242 B2
(45) Date of Patent: Nov. 12, 2019

(54) APPLICATOR AND SYSTEM FOR ADMINISTERING AND DISPENSING FLOWABLE PHARMACEUTICAL PREPARATIONS

(71) Applicant: Ramiro M. Perez, Folsom, CA (US)

(72) Inventor: Ramiro M. Perez, Folsom, CA (US)

(73) Assignee: BIOSRX, INC., Folsom, CA (US)

( * ) Notice: Subject to any disclaimer, the term of this patent is extended or adjusted under 35 U.S.C. 154(b) by 634 days.

(21) Appl. No.: 14/997,553

(22) Filed: Jan. 17, 2016

(65) Prior Publication Data

US 2016/0129228 A1    May 12, 2016

Related U.S. Application Data

(63) Continuation-in-part of application No. 14/042,588, filed on Sep. 30, 2013, now abandoned, which is a continuation-in-part of application No. 13/275,282, filed on Oct. 17, 2011, now Pat. No. 8,544,684.

(60) Provisional application No. 61/443,029, filed on Feb. 15, 2011.

(51) Int. Cl.
| | |
|---|---|
| *A61M 5/315* | (2006.01) |
| *A61M 31/00* | (2006.01) |
| *A61K 31/565* | (2006.01) |
| *A61K 31/57* | (2006.01) |
| *G01F 13/00* | (2006.01) |
| *A61M 35/00* | (2006.01) |

(52) U.S. Cl.
CPC .......... *A61M 31/00* (2013.01); *A61K 31/565* (2013.01); *A61K 31/57* (2013.01); *G01F 13/00* (2013.01); *A61M 35/003* (2013.01); *A61M 2205/19* (2013.01); *A61M 2205/582* (2013.01); *A61M 2205/583* (2013.01)

(58) Field of Classification Search
CPC .. A61M 5/31501; A61M 5/168; A61M 5/178; A61M 5/3129; A61M 5/31511; A61M 5/31525
See application file for complete search history.

(56) References Cited

U.S. PATENT DOCUMENTS

| | | |
|---|---|---|
| 2,907,496 A | 10/1959 | Carstensen |
| 3,333,740 A | 8/1967 | Waller |
| 3,616,970 A | 11/1971 | Baumann et al. |
| 3,862,748 A | 1/1975 | Grise |
| 3,873,008 A | 3/1975 | Jahn |
| 4,074,833 A | 2/1978 | Otto, Sr. |
| 4,139,127 A | 2/1979 | Gentile |
| 4,298,036 A | 11/1981 | Horvath |
| 4,363,560 A | 12/1982 | Gentile |
| 4,521,127 A | 6/1985 | Tomburo et al. |
| 4,544,083 A | 10/1985 | Schroeder |
| 4,595,124 A | 6/1986 | Duval et al. |
| 4,641,776 A | 2/1987 | Vlasek et al. |
| 4,658,993 A | 4/1987 | Vlasich |
| 4,850,516 A | 7/1989 | Seager |
| 4,865,231 A | 9/1989 | Wiercinski |
| 5,000,356 A | 3/1991 | Johnson et al. |
| 5,007,755 A | 4/1991 | Thompson |
| 5,016,782 A | 5/1991 | Pfanstiel |
| 5,025,960 A | 6/1991 | Seager |
| 5,397,178 A | 3/1995 | Konietzko |
| 5,540,361 A | 7/1996 | Fattori |
| 5,573,341 A | 11/1996 | Iaia |
| 5,725,133 A | 3/1998 | Iaia |
| 5,839,622 A | 11/1998 | Bicknell et al. |
| 5,851,079 A | 12/1998 | Horstman et al. |
| 5,947,621 A | 9/1999 | Szekely |
| 6,039,483 A | 3/2000 | Szekely |
| 6,375,047 B1 | 4/2002 | Herda |
| 6,450,720 B1 | 9/2002 | Cai |
| 7,086,564 B1 | 8/2006 | Corrigan |
| 7,213,994 B2 | 5/2007 | Phipps et al. |
| 7,303,348 B2 * | 12/2007 | Phipps ................ A61M 35/003 222/390 |
| 7,399,113 B2 | 7/2008 | Konietzko |
| 7,751,934 B2 | 7/2010 | Konietzko |
| 7,879,830 B2 | 2/2011 | Wiley |
| 7,946,780 B2 | 5/2011 | Zhang |
| 8,292,532 B2 | 10/2012 | Nasu et al. |
| 2004/0118879 A1 | 6/2004 | Konietzko |

(Continued)

FOREIGN PATENT DOCUMENTS

| | | |
|---|---|---|
| WO | WO93/23156 | 11/1993 |
| WO | WO02/26369 | 4/2002 |
| WO | WO02/087986 | 11/2002 |

OTHER PUBLICATIONS

Holtorf, K et al. Holtort Medical Group, "The Bioidentical Hormone Debate: Are Bioidentical Hormones (Estradiol, Estill, and Progesterone) Safer or More Efficacious than Commonly Used Synthetic Versions in Hormone Replacement Therapy?" Torrance, CA: US (2009).

Johnson, Michael L. and Veldhuis, Johannes D., "Quantitative Neuroendocrinology: Methods in Neuroscience." San Diego, CA: US (1995).

Lokkegaard, E et al. Institute of Public Health, University of Copenhagen, "Hormone therapy and risk of myocardial infarction: a national register study." Copenhagen, DK (2008).

Scharfman, H et al MacLusky, N, "Estrogen-Growth Factor Interactions and Their Contributions to Neurological Disorders." Orangeburg, NY: US (2009).

*Primary Examiner* — Micah Paul Young
(74) *Attorney, Agent, or Firm* — Inventive Law Inc.; Jim H. Salter (57) ABSTRACT

Embodiments are disclosed for an applicator used for inserting flowable pharmaceutical preparations into a body cavity, an adapter for connecting a jar to a cavity dispenser, a jar dispenser with a nozzle for automated transferring and dispensing of flowable pharmaceutical compositions, and a metered dial-dispenser configured to connect to a cavity dispenser for humans and animals.

18 Claims, 10 Drawing Sheets

(56) References Cited

U.S. PATENT DOCUMENTS

2010/0217176 A1* 8/2010 Carrara .................. A45D 34/04
                                                                   604/20
2012/0205000 A1   8/2012  Phipps
2012/0269029 A1  10/2012  Konietzko

* cited by examiner

APPLICATOR AND SYSTEM FOR ADMINISTERING AND DISPENSING FLOWABLE PHARMACEUTICAL PREPARATIONS

REFERENCE TO PRIORITY PATENT APPLICATIONS

The present application is a non-provisional continuation-in-part patent application claiming priority to U.S. patent application Ser. No. 14/042,588, filed on Sep. 30, 2013; which is a non-provisional continuation-in-part patent application claiming priority to U.S. patent application Ser. No. 13/275,282, filed on Oct. 17, 2011, now U.S. Pat. No. 8,544,684; which is a non-provisional U.S. patent application claiming priority to Ser. No. 61/443,029, filed on Feb. 15, 2011. The present non-provisional continuation-in-part patent application claims priority to the referenced patent applications, which are hereby incorporated by reference herein in their entirety.

TECHNICAL FIELD

The various embodiments described herein relate to an applicator for inserting flowable pharmaceutical preparations into a body cavity, an adapter for connecting a jar to a cavity dispenser, a jar dispenser with a nozzle for automated transferring and dispensing of flowable pharmaceutical compositions, and a metered dial-dispenser configured to connect to a cavity dispenser for humans and animals.

COPYRIGHT

A portion of the disclosure of this patent document contains material that is subject to copyright protection. The copyright owner has no objection to the facsimile reproduction of the patent document or the patent disclosure, as it appears in the Patent and Trademark Office patent files or records, but otherwise reserves all copyright rights whatsoever. The following notice applies to the software and data as described below and in the drawings that form a part of this document: Copyright 2014-2016 Ramiro M. Perez, All Rights Reserved.

BACKGROUND

One of the greatest challenges patients face today, is the ability to self-administer accurate and precise oral, topical, rectal, and vaginal dosages of prescribed flowable medications. The main culprit being the limitations posed by commercially available delivery systems. Furthermore, measuring the correct dosage of flowable drugs to be applied through these routes of administration in the older patient population, requires their ability to see the small, dye printed, faint numbers on the plunger of the applicator as it is with the prior arts. Similarly, self-application of an accurate and precise flowable dosage by the visually impaired patient population is also not presently possible. In addition, feedback mechanisms that ensure proper dosing in a metered, and tactile fashion are also non-existent. The ability to preload flowable custom drug dosages into a cavity applicator from piston driven jar dispensers, and also to protect from evaporation and contamination are also not presently available.

Standard vaginal applicators today generally consist of two parts: Barrel and plunger. Some companies distribute the vaginal applicator without applicator caps, while others do include them. Variations in vaginal applicators may comprise three components. Barrel, cap, and a plunger with a fused piston at the first end. The applicators generally are molded then delivered to a printing company where the plunger is imprinted with dosing ruler so that the patient would be able to read the information and apply the proper amount. Further handling of the parts beyond its manufactured institution is generally a problem for manufacturers as it increases costs, as well as the likelihood of damage and contamination of the parts.

Vaginal hormone preparations are generally packaged in plastic and aluminum tubes and used by older female patients generally during their perimenopausal, menopausal, and postmenopausal years of life. The patient is instructed to connect the tube to the vaginal applicator by screwing-on the applicator to the tube. Next, the patient applies pressure to the tube in order to fill the chamber of the vaginal applicator and causes the plunger of the applicator to rise. Once the desired dose is measured, the patient unscrews the applicator from the tube and inserts the measured dosage vaginally.

Expert physicians with advanced training in the functional and anti-aging community have repeatedly expressed that the present vaginal dispensers are too long to be properly inserted into the desired areas of the vaginal canal of women seeking hormone replacement therapy. In fact, in several cases the excess in length has caused trauma to the cervix and fornix. Lastly, the common applicator's shape is presently sub-optimal, painful, and it often lacks adequate anti-slippery holding regions, and depth indicators.

A delivery system that would offer visual, tactile, and metered dispensation is highly desirable to either transfer the flowable composition directly into the desired body area, or to a secondary applicator designed for the body cavities. Furthermore, a cavity dispenser that would offer clearly visible and tactile dosing segments with dosing tabs to facilitate feedback mechanisms is highly desirable, especially in the visually impaired population. These individuals would benefit from a reassuring dosing system that would allow them to feel the dosing segments on the plunger for measuring the proper dosage with their hands and fingers prior to applying the dosage.

SUMMARY

The various embodiments described herein eliminate the necessity of imprinting on the plunger, as it has been done for decades. This novel applicator is constructed with largely visible dosing tabs and inter segments to the naked eye. Furthermore, in cases where the eyesight may be impaired, the dosing tabs and inter-segments are also easily identified by the sense of touch. Additionally, above each segment, an extruded number is also positioned in sequential numerical order to indicate the amount being applied. Another advantage the various embodiments described herein offer, is the ability to preload these applicators with multiple volumetric quantities such as 1, 2, 3, or 4 milliliters as necessary for the compounding laboratory.

A length-conscious cavity applicator for delivering flowable pharmaceutical preparations for hormone and other therapies built with visual, feedback, tactile, and metered mechanisms is disclosed. The ability to transfer flowable compositions from metered and non-metered piston-driven apparatuses into the smaller chambered cavity applicators through different types of connecting configurations or removable adapters are also disclosed herein. Lastly, a piston driven jar dispenser with a nozzle and cap configured for manual and automated dispensing is also disclosed herein.

With regard to the various embodiments described herein, a cavity applicator is provided for delivering accurate and precise dosages of flowable pharmaceutical preparations into the cavity of a human or animal. The cavity applicator comprises the hollow body to store the composition, plunger to push the contents inside the body cavity, and a cap to retard evaporation of the contents inside. The cavity applicator is loaded by larger piston-driven metered and non-metered containers directly or via adapter. The non-metered piston-driven jar dispensers consist of a barrel, a lid with a center outlet, and a push-piston to drive the contents to a secondary delivery system via a removable nozzle, or to a cavity applicator via a removable adapter. The metered container consists of a cap, barrel, dispensing lid with a central outlet, and a rotatable base that is coupled to a screw that causes a piston to move upwards; thereby, also driving the contents into the desired chamber of the cavity applicator.

BRIEF DESCRIPTION OF THE DRAWINGS

The various embodiments are illustrated by way of example, and not by way of limitation, in the figures of the accompanying drawings in which.

DETAILED DESCRIPTION

In the following description, for purposes of explanation, numerous specific details are set forth in order to provide a thorough understanding of the various embodiments. It will be evident, however, to one of ordinary skill in the art that the various embodiments may be practiced without these specific details.

In the various embodiments described herein, example embodiments relate to an applicator for inserting flowable pharmaceutical preparations into a body cavity, an adapter for connecting a jar to a cavity dispenser, a jar dispenser with a nozzle for automated transferring and dispensing of flowable pharmaceutical compositions, and a metered dial-dispenser configured to connect to a cavity dispenser for humans and animals. In the various embodiments described herein, example embodiments relate to length-conscious cavity applicator for delivering flowable pharmaceutical preparations for hormone and other therapies built with visual, feedback, tactile, and metered mechanisms. The ability to transfer flowable compositions from metered and non-metered piston-driven apparatuses into the smaller chambered cavity applicators through different types of connecting configurations or removable adapters are also disclosed herein. Lastly, a piston driven jar dispenser with a nozzle and cap configured for manual and automated dispensing is also disclosed herein. The details of these example embodiments are provided below.

Cavity Applicator and Cap

Figure 1:
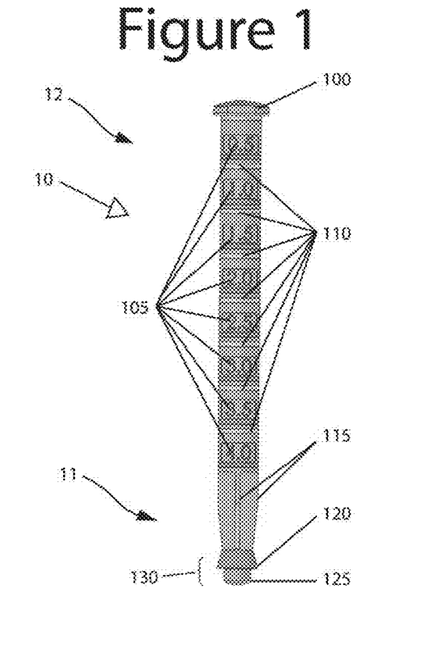
FIG. 1 is a side view of the plunger; the top end is the distal end, and bottom end is the proximal end.
Figure 2:
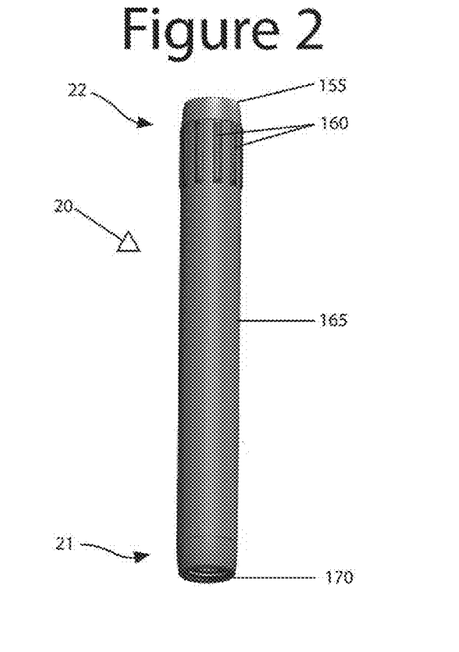
FIG. 2 is a side view of the barrel; the top end is the distal end, and bottom end is the proximal end.
Figure 3:
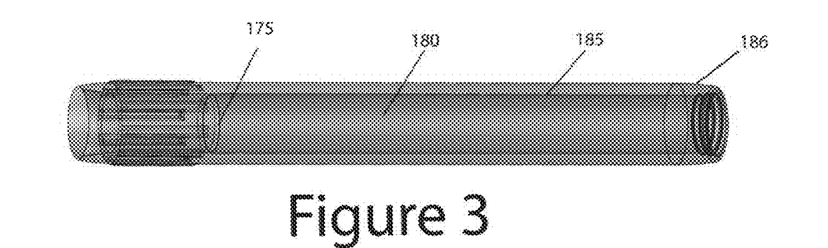
FIG. 3 is a side view of the barrel with a threaded end on its proximal end.
Figure 4:
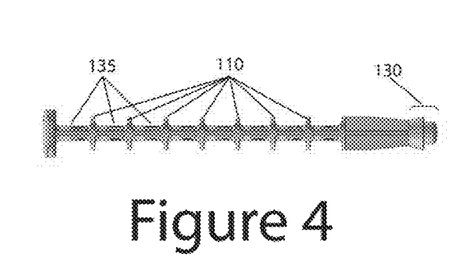
FIG. 4 is a side view of the plunger with a 90 degree axial rotation with respect to the view shown in FIG. 1.
Figure 5:
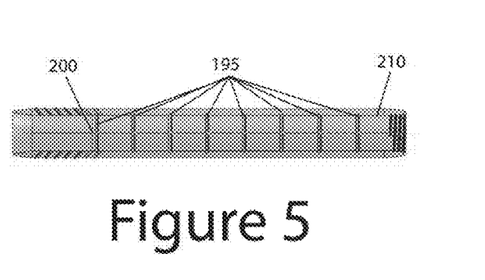
FIG. 5 is a cross sectional view of a barrel with calibrated rest segments.

FIGS. 1 through 11 depict an example embodiment of the cavity applicator 300. We will solely make references to a cavity applicator from here on, but it is to encompass vaginal, rectal, oral, and other like sites of application in humans and animals. Furthermore, the applicator may also extend beyond the cavity sites of application to topical or transdermal delivery sites. In one embodiment, the plunger 10 that has been constructed as a robust dome seal complex 130 on its proximal end 11 connected through structural guiding ribs 115 to a segmented dosing area and a digit trigger 100 at the distal end 12. As the consumer exerts force on the digit trigger 100 of the plunger 10, it slides through the inner walls of the barrel 20. Meanwhile, at the proximal end 21 of the barrel 20, the piston seal 120 pushes the contents inside the chamber to exit through the outlet into the desired body cavity. The amount dispensed is equivalent to the number of dosing segments cleared against the distal end 22 of the barrel 20. As illustrated in FIG. 1, the plunger 10 is exposed in a side view where the dome-seal complex 130 comprises the piston seal 120 and the dome tip 125 at the proximal end 11 of plunger 10. The structural guiding ribs 115 make way to the dosing tabs 110 and to the inter-segments 135. Each inter-segment 135 houses an extruded number 105 to denote volume to be dispensed in milliliters. The preferred numbers are arranged sequentially, starting from the lowest at the top (0.5) and the highest at the bottom (4.0). Other fractional segments may be possible to configure. Likewise, the dosing interval 140 can be manufactured to be larger or smaller, and it will likely vary the size of the cavity applicator.

Figure 21A:
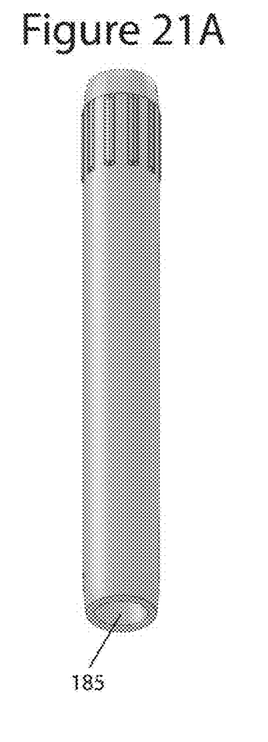
FIG. 21A is a bottom-side view of the barrel of the cavity applicator exposing the proximal end of the barrel, and the inner wall; note, there are no circular rims or threads in this configuration.
Figure 21B:
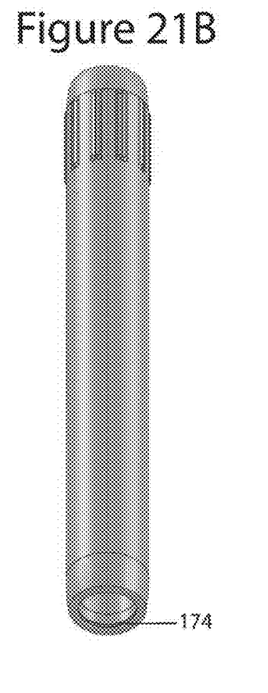
FIG. 21B is a bottom-side view of the barrel of the cavity applicator exposing the proximal end of the barrel, inner side wall, and a rim.

The barrel 20 of the cavity applicator 300 comprises an elongated, double-walled, hollow cylinderlike design. Other shapes may also be possible to manufacture if desired. The proximal end 11 of the plunger 10 gets inserted through the distal edge window 155 of the barrel 20, past the one way ramp 175 sliding through the inner wall 185 of the barrel 20. The barrel 20 has a thumb grip and depth indicator 160 at its distal end 22. Therefore, as it gets inserted to the depth where the thumb grip and depth indicator resides 160, the consumer will likely feel the ribs around the circumference of the applicator entering the cavity via sensory feedback mechanisms. The barrel body 165 can also be used to insert the applicator if desired for a shallower depth. In one of the embodiments as seen on FIG. 6 through 7B and FIG. 12 through 13, the proximal threaded end 170 of the barrel 20 screws to the distal screw 240 of the adapter 350. However, on a separate embodiment, FIG. 21A displays the proximal inner wall of the barrel 185 without threads or rims, and the mating takes place simply through a pressured slide in and slide out connecting mechanism. In contrast, FIG. 21B displays a rim indent 174 on the proximal end 21 of the barrel 20. Therefore, the proximal end 21 of the barrel 20 will slide into its mating counterpart, and then it will snap into place for a tighter connectivity.

Figure 8:
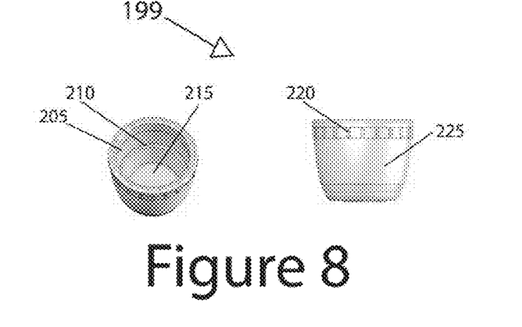
FIG. 8 depicts a top view and a side view of a non-threaded cavity applicator cap.
Figure 9:
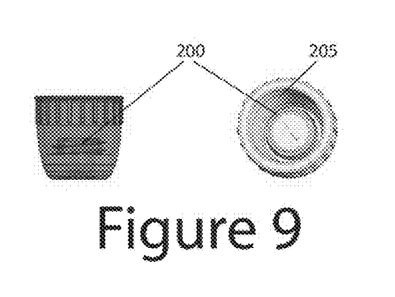
FIG. 9 depicts a side view and a top view of a threaded applicator cap.

In reference to FIG. 8, the proximal outer wall 186 of the barrel 20 slides through the inner side wall 205 of the cap 199 until it reaches the stopper 210 and it is bounded by the inner bottom wall of the cap 215. On a separate embodiment, FIG. 9 presents a screw-on version of the lid, where the inner bottom wall 215 of the cap houses a threaded screw 200 at its center, configured to screw with the proximal threaded end 170 of the barrel 20.

Figure 6:
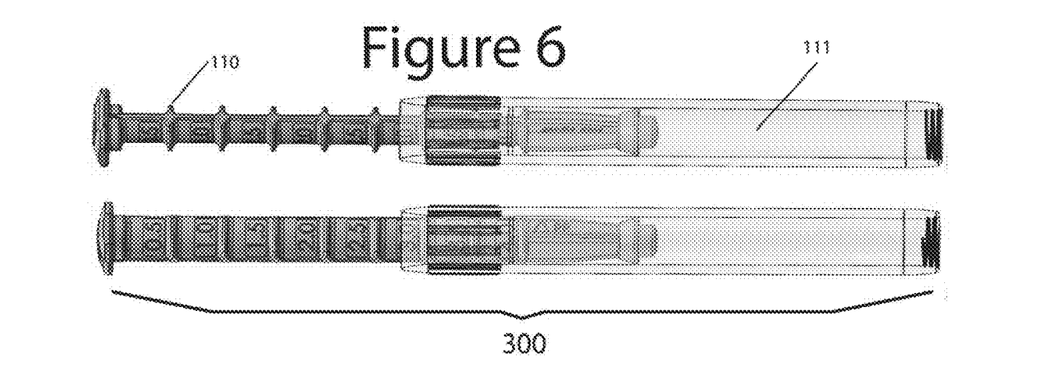
FIG. 6 depicts a side view of a pair of semi-transparent barrels with the plungers inserted (Applicator caps excluded)
Figure 7A:
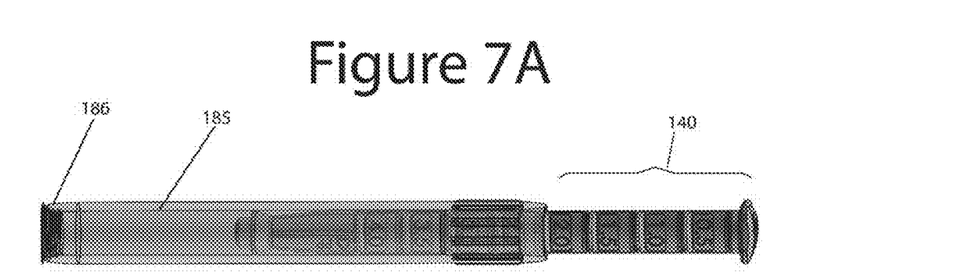
FIG. 7A is a side view of the barrel and plunger pushed to the 2.0 dosing interval (Applicator cap excluded)
Figure 7B:
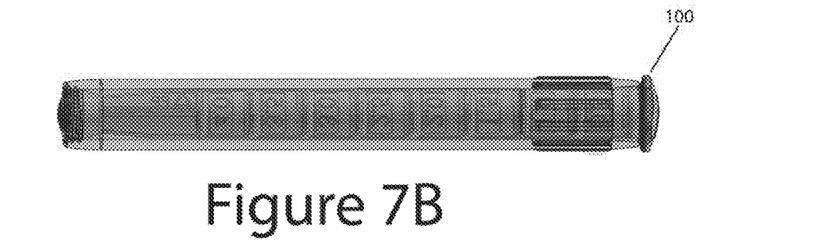
FIG. 7B is a side view of the barrel with the plunger completely inserted into the barrel.
Figure 10A:
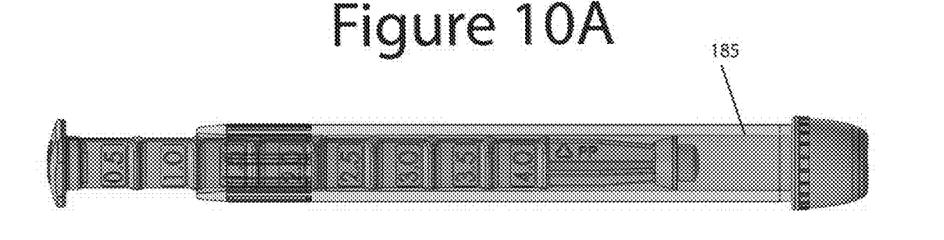
FIG. 10A is a side view of the complete cavity applicator assembly without calibrated rest segments or circular ramps.
Figure 10B:
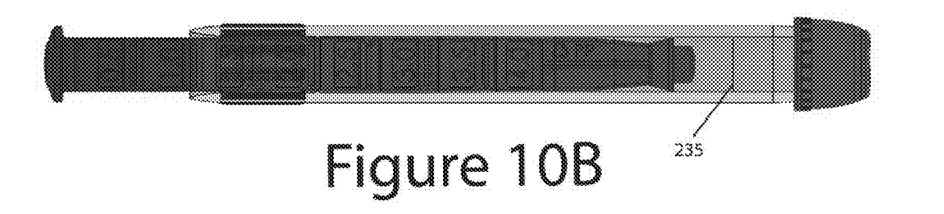
FIG. 10B is a side view of the complete applicator assembly with circular ramps.
Figure 11:
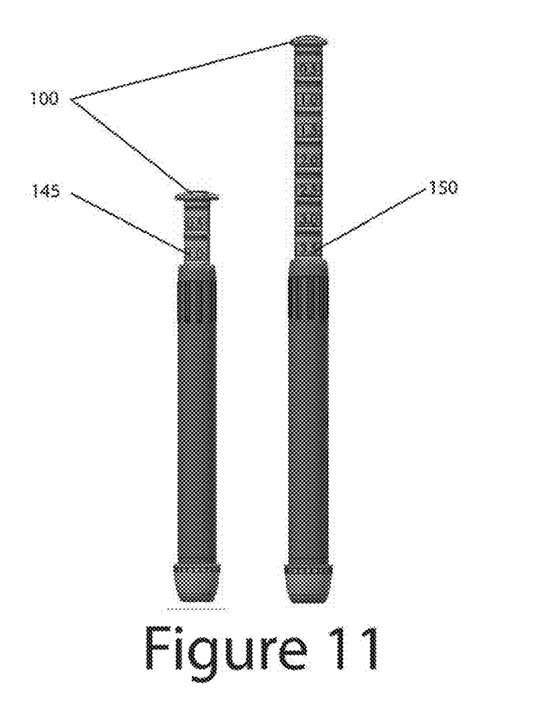
FIG. 11 depicts a side view of two complete applicator assemblies with different dosing intervals.

The barrel 20 may be configured to contain large and small volumetric quantities as generally desired, with a preferred maximum capacity between four to five milliliters and a preferred length between 100-110 millimeters. The plunger as illustrated in FIGS. 6 through 7B also has a preferred length between 100-110 millimeters. These metric values can be modified based on consumer and physician demands. Generally, a loading dosage ranging from two to four milliliters is first prescribed for the first weeks of therapy. Then, a smaller maintenance dosage is prescribed ranging from half to one milliliter. The example embodiments of FIGS. 6, 7A, 7B, 10A, 10B exhibit the applicator 300 configured with eight inter-segments 135 each bounded by its respective extruded visual and tactile dosing tab 110. Each dosing tab 110 is preferably configured to deliver a half-milliliter of pharmaceutical preparation and the cavity applicator shown is configured with a four milliliter total capacity. Alternatively, the applicator may be configured with larger or smaller dosing increments such as 0.25 ml or 0.125 ml based on consumer and physician demands. On a separate embodiment, FIG. 10A displays the barrel of the applicator without any circular segments 235. In contrast, on a separate embodiment, the inner wall 185 of the barrel 20 is equipped with a plurality of calibrated small circular extruded ramps 235 or circular hollow segments 195 as shown on FIG. 10B and FIG. 5 alongside the inner wall 185 of the barrel 20. Each of these ramps or segments represent a predetermined dosage which may be applied by the consumer. The ramps and rest segments facilitate feedback mechanisms and indicate a positional frame of reference of how much volumetric dosage has been applied. FIG. 10B displays eight calibrated circular rest segments 235 configured to interact with the piston seal 120 of the plunger 10 thus creating a feedback mechanism for the end user to indicate the dosage applied. The calibrated circular segments 195 and circular extruded ramps 235 of the barrel 20 of the cavity applicator 300 correspond with the linear displacement of the dosing tabs 110 on the plunger 10 against the distal edge window 155 of the barrel 20.

Figure 12:
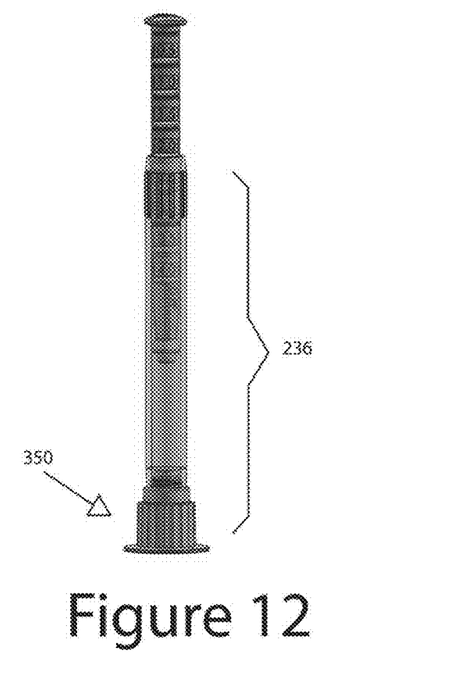
FIG. 12 depicts the plunger and barrel attached to an adapter.
Figure 13:
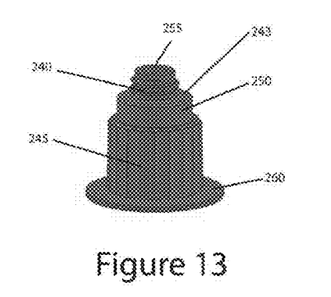
FIG. 13 is a side view of the adapter with a screw on its distal end.
Figure 14:
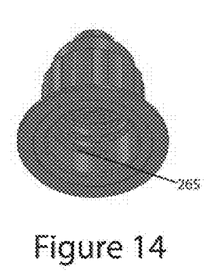
FIG. 14 depicts a bottom-side view of the adapter exposing the inner threads.
Figure 15:
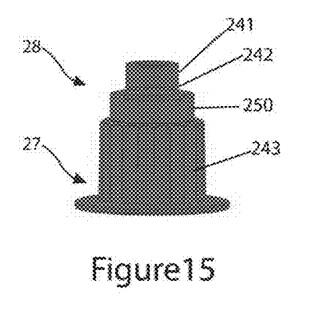
FIG. 15 depict a side view of the adapter with an adapter rim at the distal end.
Figure 16:
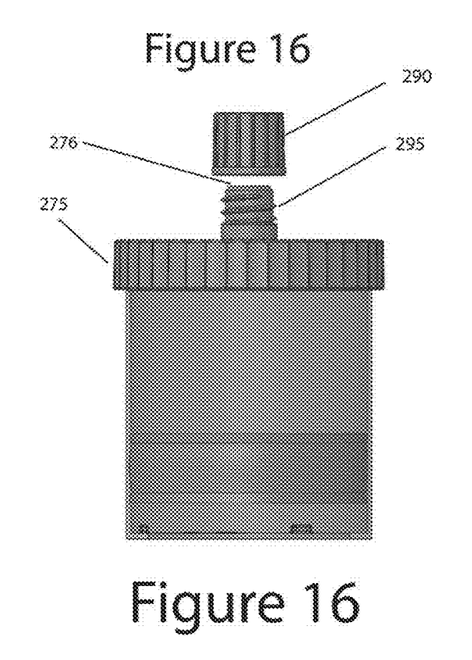
FIG. 16 is a side view of the jar with piston and a screwable lid attached; the screwable cap is also displayed right above the lid.
Figure 22A:
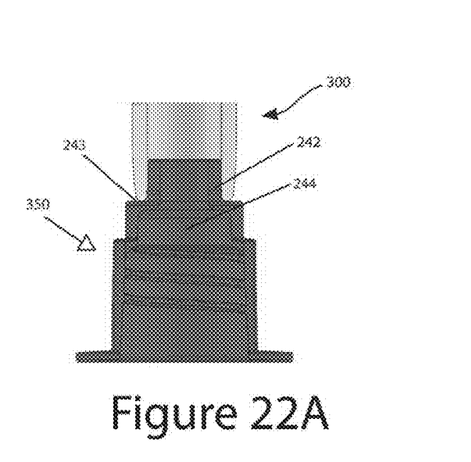
FIG. 22A depicts a cross section side view of the adapter attached to the cavity applicator and a rim at its distal end; the applicator slides into the adapter until it snaps into place for a tighter connection.
Figure 22B:
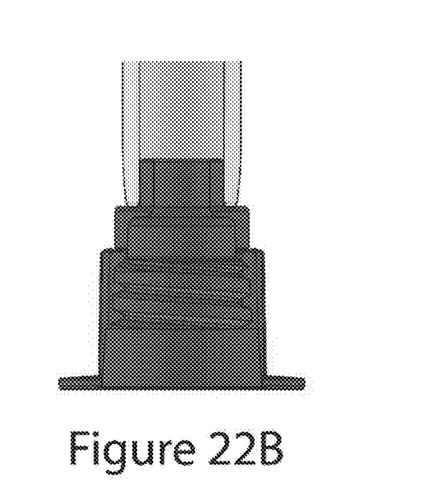
FIG. 22B depicts a cross-sectional side view of the adapter attached to the cavity applicator; the cavity applicator is configured to slide into and out of the adapter.
Figure 29:
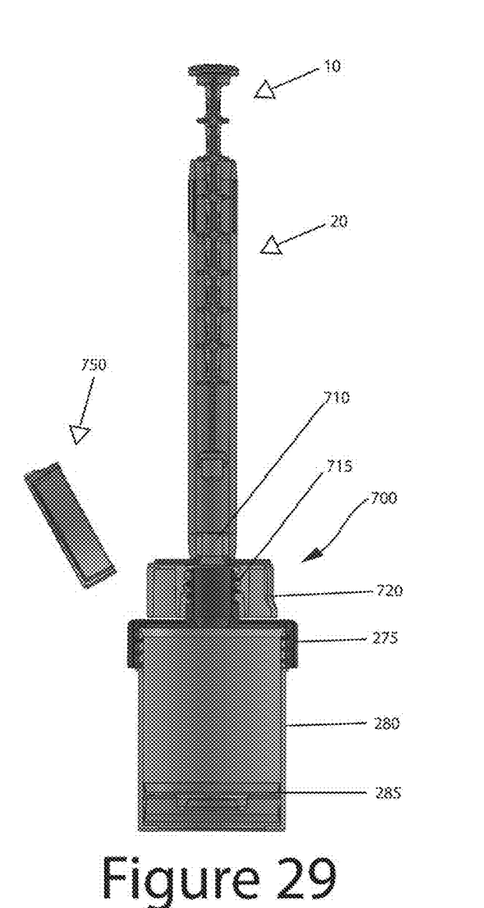
FIG. 29 is a side cross-sectional view of the dispenser jar, flip-cap adapter, and cavity applicator.
Figure 30:
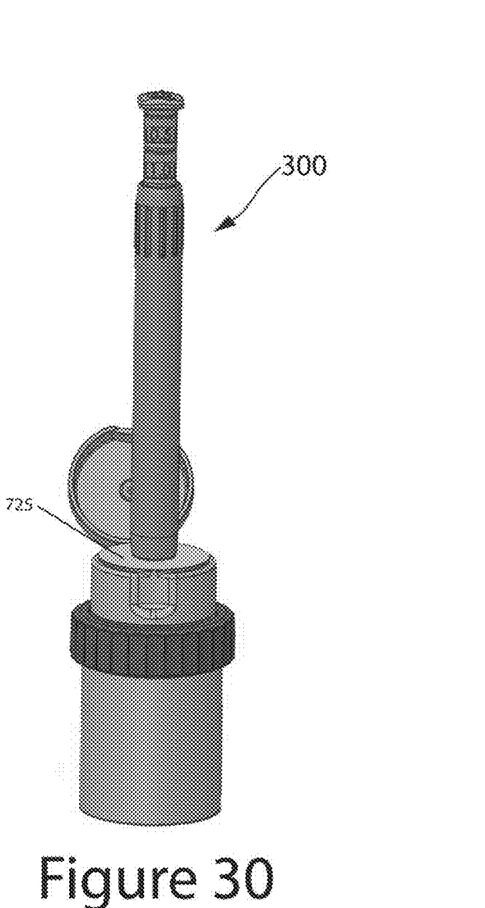
FIG. 30 is a side view of the dispenser jar, flip cap adapter, and cavity dispenser.

In another embodiment, FIG. 12 shows the mating mechanism between the cavity applicator 300 and standard tube may be by means of a screw system. The cavity applicator 300 may screw to a tube, adapter 350, or directly to a jar dispenser 400 that would have the proper mating system configured. Once the cavity applicator 300 is connected, then the larger container fills the smaller container. As the cavity applicator 300 gets filled, the plunger 10 rises, consistent with the cream or gel is inside the barrel 20 and corresponding to the dosage displayed on the plunger 10. Alternatively, in separate embodiment as seen in FIG. 22B, the cavity applicator 300 mates with the adapter 350 via a slide in and slide out connecting mechanism. Similarly, in a separate embodiment, FIG. 22A shows the mating between the adapter 350 and the cavity applicator 300 being a slide and snap connecting mechanism. The added snap mechanism facilitates a tighter fit when necessary. Lastly, on a separate embodiment, FIG. 29 and FIG. 30 show similar connecting mechanisms as described above, but the adapter 700 further comprises a flip cap to retard evaporation. The slide and snap mechanism would mate the applicator to the tube, jar, or metered dispenser. The proper amount of pressure would simply maintain the two parts attached.

Adapters-Dispenser Jar-Cavity Applicator

In the embodiments described below, the adapter has been configured to slide, snap, or screw to the lid of larger containers and dispensing jars to enable the transferring of flowable compositions into the small chamber of cavity dispensers. Furthermore, the adapter may feature semi-threaded characteristics to avoid the unscrewing process of the molded parts. Lastly, the adapter is configured to house a cap or flip cap on its distal end to retard evaporation of the contents inside the dispensing jar. With references to the embodiments as shown on FIG. 26, the user presses on the piston 285 of the jar dispenser 400 from the bottom with a thin rod or fingers, and the cream or gel preparation exits the chamber of the dispenser jar 400 through the center outlet 276 of the removable lid 275 and it continues its path through the inner chamber 244 of the adapter 350, and then it enters the inner chamber 111 of the cavity applicator 300. One notable advantage of this assembly, is the ability for the user to transfer the flowable preparation back into the dispenser jar 400 if desired; especially on cases where a larger than needed dosage was transferred into the applicator 300 by mistake.

Alternatively, the embodiments of FIGS. 12 through 15 describe the adapter 350 which facilitates the connection of the jar dispenser 400 to the cavity applicator 300 where the outlet of the adapter 255 connects to the cavity applicator's barrel 20 by screwing the threaded end 170 of the barrel 20 with the threaded screw of the adapter 240. In a preferred embodiment, the outlet 255 of the adapter 350 connects to the barrel 20 of the cavity applicator 300 by sliding the top outer side wall 241 of the adapter 350 into the inner wall 185 of proximal end 21 of the barrel 20.

Figure 17:
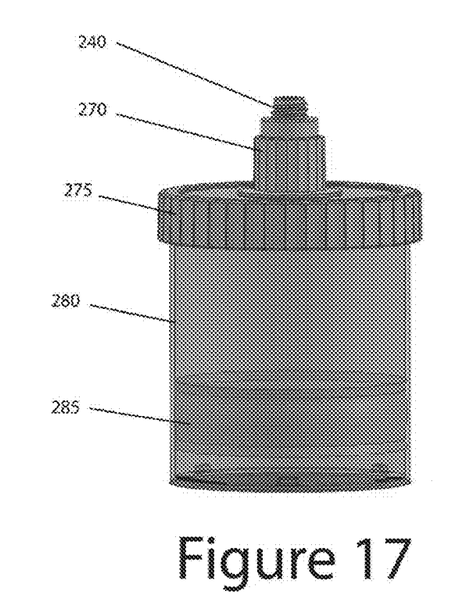
FIG. 17 is a side view of the jar with piston, barrel, screwable lid, and the screwable adapter attached.
Figure 18:
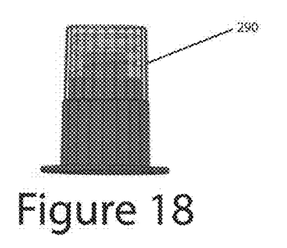
FIG. 18 depicts side view of the screwable adapter and screwable cap; although the cap is threaded on the inside, the external attachment to the cap takes place through slide-in, slide-off mechanisms.
Figure 19:
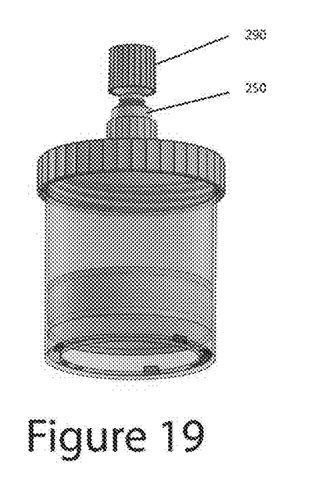
FIG. 19 depicts a side view of the barrel, piston, screwable lid with a central outlet, screwable adapter, and cap.
Figure 31:
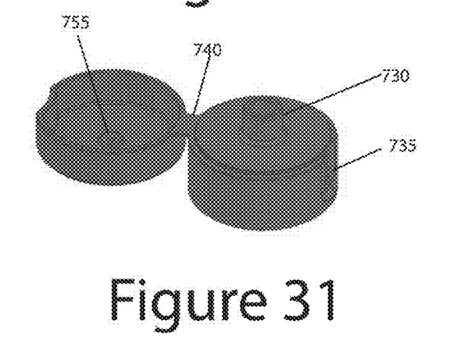
FIG. 31 is a top side view of the flip cap adapter.
Figure 32:
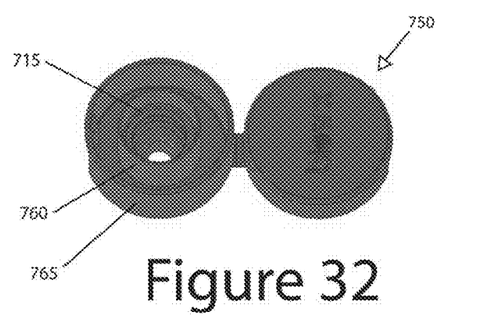
FIG. 32 is a top side view of an inverted flip cap adapter.

Furthermore, at the proximal end 27 of the adapter 350 lies the internal threaded cavity 265 of the said adapter 350 which screws to the threaded outlet 295 of the removable lid 275 which is screwed to the jar dispenser 400 as seen on FIGS. 17 and 19. Similarly, on a separate embodiment as shown on FIGS. 31 and 32, the internal threaded cavity 715 is shown with a longer inner rim 760 around it. Also, a thumb indent 735 is evident, stemming from the outer wall of the outer side rim 765.

Therefore, when the consumer exercises pressure on the piston 285 of the jar dispenser 400, as shown in FIGS. 17, and 19 the piston 285 travels and the contents inside the jar dispenser 400 exit through outlet 276 of the lid 275 and continue to travel through the inner chamber 244 of the adapter 350 into the inner chamber 111 of the barrel 20. As result, the plunger 10 attached to the barrel 20 of the cavity applicator 300 rises as the chamber 111 of the applicator 300 gets filled with the cream or gel preparation. If too much cream gets transferred, the consumer simply measures the correct amount with the dosing tabs 110 of the plunger 10 and presses the desired dosage. The cream or gel preparation travels back to the jar dispenser 400. In addition, any excess may also be discarded if desired. Once the desired dosage has been measured with the dosing tabs 110 of the plunger 10, the consumer detaches the cavity applicator 300, and inserts it into the cavity to the desired depth. The consumer presses the digit trigger 100 of the plunger 10 all the way down to apply the total measured amount of pharmaceutical preparation.

Figure 26:
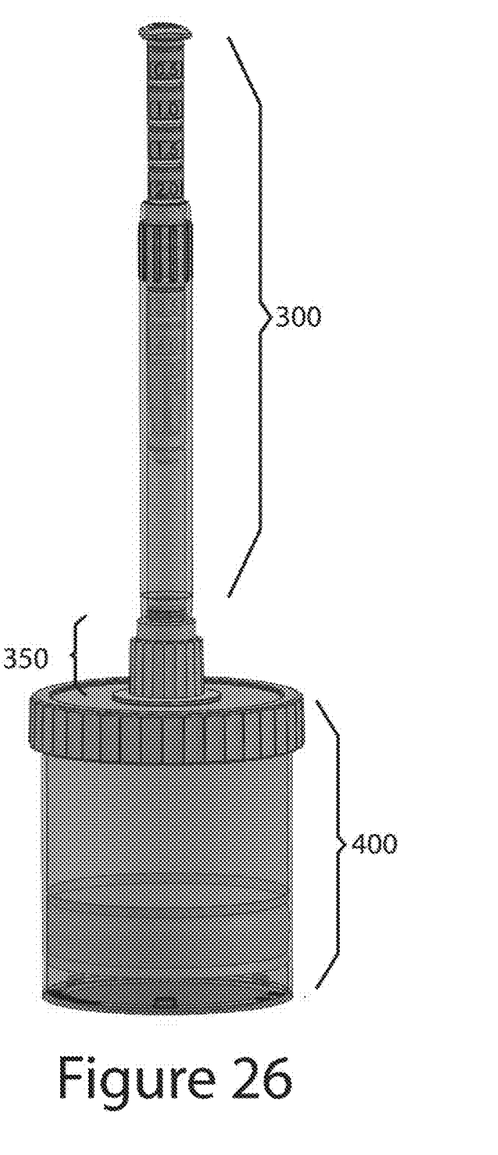
FIG. 26 is a side view of the jar dispenser, adapter, and cavity applicator.

In the embodiment as shown on FIGS. 22B and 26, the jar dispenser 400 has the ability of being connected to the cavity applicator 300 by means of the adapter 350 as previously mentioned. Likewise, on a separate embodiment, FIGS. 29 through 32 displays the jar dispenser 400 connected to the cavity applicator 300 by means of a flip-cap adapter 700. This adapter is similar to the adapter of FIGS. 13 through 15, 22B, and 26; but, it is configured with a flip cap to retard evaporation and to make it easier to access the inner contents. Furthermore, this flip cap adapter 700 also connects to the cavity applicator 300 by means of slide, snap, or screw mechanisms as previously demonstrated.

The barrel 20 of the cavity applicator 300 slides over the rim outlet 730 of the flip cap 700 and connects snugly. When the piston 285 of the jar dispenser 400 is pushed upwards towards its distal end, the flowable composition passes through the inner chamber of the flip cap adapter 700, and continues into the inner chamber 111 of the cavity applicator 300.

Figure 27:
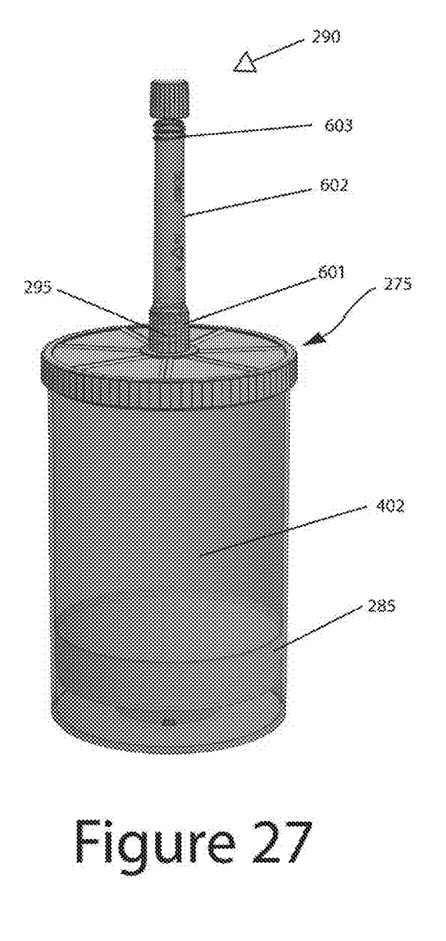
FIG. 27 is a side view of the dispenser jar, nozzle, and cap.
Figure 28:
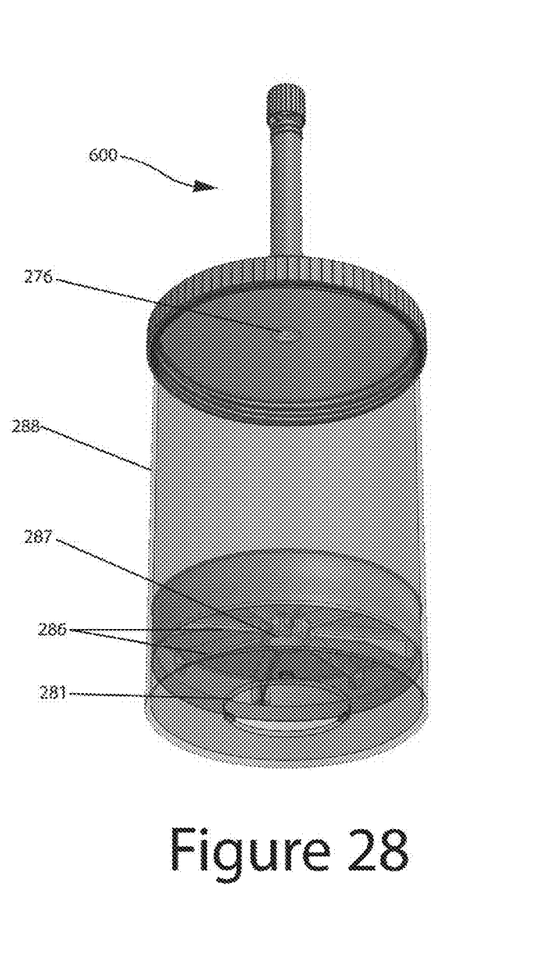
FIG. 28 is a bottom side view of the dispenser jar, nozzle, and cap.

On a separate embodiment, FIG. 27-28 exhibits a much larger dispenser jar 400. These dispenser jars 400 are generally configured for automated transfers, and a removable nozzle 600 is generally attached to facilitate the transfer from the larger dispenser jar (FIG. 27-28) into smaller jars and like containers.

Metered Dial Dispenser (Ticker and Cavity Applicator)

Figure 20A:
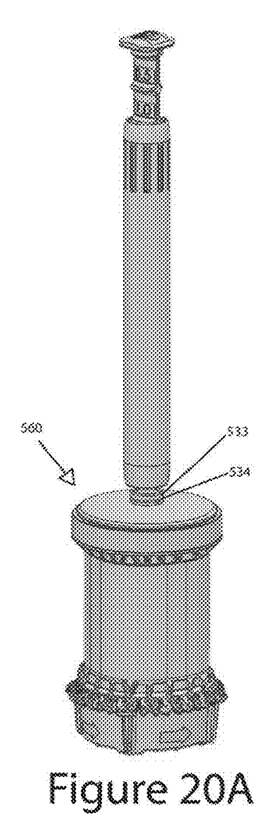
FIG. 20A is a side view of the bi-audible, bi-tactile, visual metered-dose applicator with the barrel and plunger of the cavity applicator right above it; the connection configured in this illustration is via a combined slide and snap mechanism.
Figure 20B:
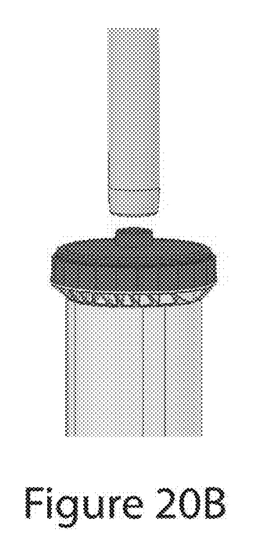
FIG. 20B is a side view of the bi-audible, bi-tactile, visual metered-dose applicator with the barrel and plunger of the cavity applicator right above it; the connection configured in this illustration is solely via a slide mechanism.

FIGS. 20A, 20B, and 23 through 25 refer to the bi-audible, bi-tactile, and visual applicator described in U.S. Pat. No. 8,544,684 (to which priority is claimed) with further modifications to its dispenser lid 560 to accommodate the attachment of a cavity applicator through slip, snap, screw, or a combination of more than one connecting mechanism. Furthermore, the dispenser lid 560 of the metered dial dispenser 500 can also be configured to mate with a silicon, rubber, or other soft material adapters to assist in the application to sensitive body areas of humans or animals. FIG. 20A is a side view of the metered dial-dispenser 500 attached to a cavity applicator 300 by combined means of Slip-On and Slip-Off and Snap-On and Snap-Off connecting mechanisms. However, the cavity applicator 300 has capabilities of being fully attached to the metered dial-dispenser 500 solely through its slip-on and slip-off mechanism as shown on FIG. 20B.

Figure 23:
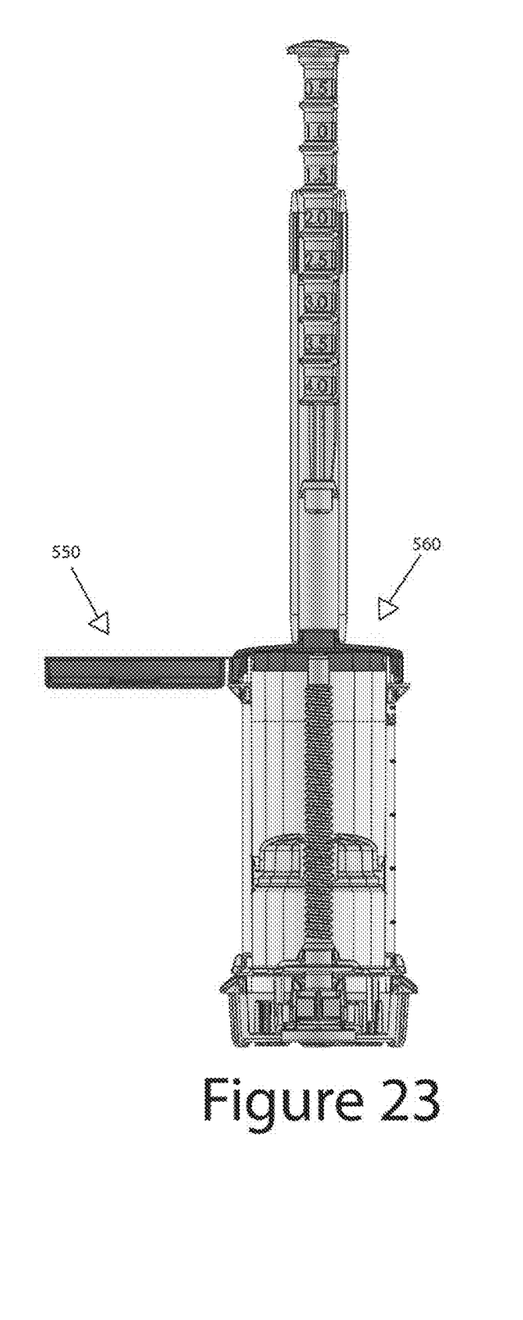
FIG. 23 is a cross-sectional side view of the bi-audible, bi-tactile, visual metered-dose applicator slipped into the barrel of the cavity applicator; a cross-section of the plunger is also shown as well as a flip cap.

Next, FIG. 23 is a cross-sectional, side view of the metered dial-dispenser displaying a flip cap 550 to retard evaporation and the dispenser lid 560 configured to mate with the cavity applicator 300 through a collaborative slip and snap connecting mechanism. In this embodiment, the proximal end 21 of the barrel 20 of the cavity applicator 300 slips in through the external wall of the outlet 533 and then it snaps-onto place by means of the outlet rim 534 of the dispenser lid 560 of the metered dispenser 500, connecting to an optional rim indent 174 of the cavity applicator 300 to cause an even tighter connectivity.

Figure 24:
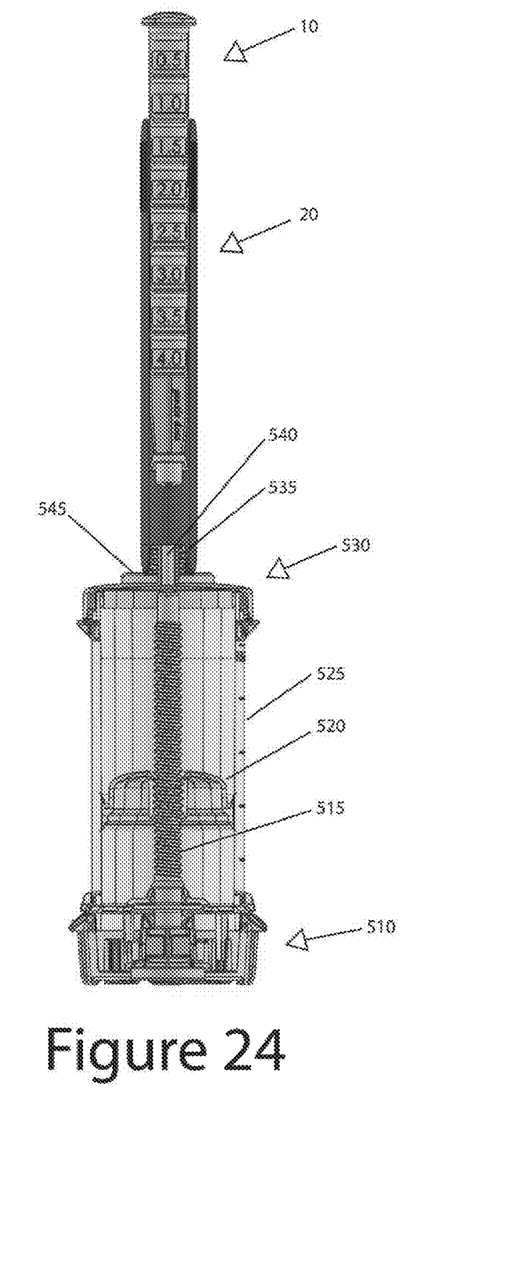
FIG. 24 is a cross-sectional side view of the bi-audible, bi-tactile, visual metered-dose applicator screwed to the barrel of the cavity applicator; a cross section of the plunger is also shown.
Figure 25:
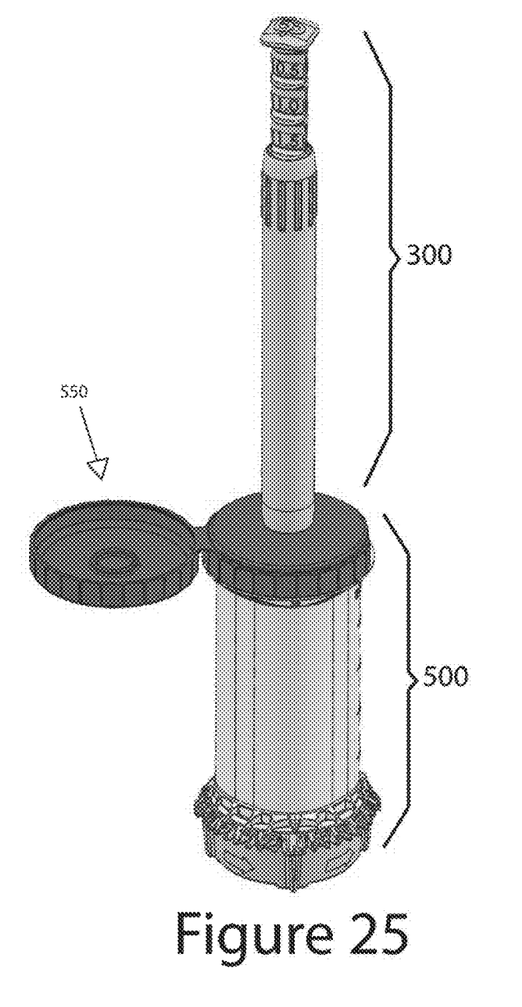
FIG. 25 is a top side view of the bi-audible, bi-tactile, and visual metered-dose applicator connected to the barrel of the cavity applicator; as the dial of the metered-dose applicator rotates clockwise by 30 clicks (540 degrees), an internal piston rises and the flowable composition gets transferred to the chamber of the cavity applicator; the plunger on top of the barrel is set to deliver a 1.5 gram volumetric dosage of flowable pharmaceutical composition.

In a separate embodiment, FIG. 24 is a cross-sectional, side view of the metered dial-dispenser screwed to a cavity dispenser. As described in U.S. Pat. No. 8,544,684, the base 510 of the metered dial-dispenser is coupled the screw 515. Clockwise rotation of the base 510 causes the screw to rotate which drives the piston 520 upwards. Contents inside the chamber of the barrel 525 exit through the outlet 540 of the dispenser lid 530. Furthermore, the threaded outlet 535 of the dispenser lid 560 connects to the proximal threaded end 170 of the barrel 20 of the cavity applicator 300. As the flowable contents enter the inner chamber of the cavity applicator, the plunger rises and the dosing interval 140 is consistent with the axial displacement of the base of the metered dial-dispenser. In other words, five clicks of the base 510 of the metered dial-dispenser 500 correspond to a 90 degree axial rotation, which, also correspond to a ¼ milliliter of flowable cream or gel preparations being transferred to the chamber of the cavity applicator 300. The end user then unscrews the cavity applicator 300, then applies the medicament as instructed.

In various embodiments as described herein, example embodiments include at least the following examples.

An adapter comprising: an outlet for a flowable pharmaceutical composition to exit or to be transferred to a secondary chamber; an inner chamber formed when the adapter is connected to two independent dispensing systems; an internal threaded or semi-threaded area on a proximal end of the adapter; an unthreaded or threaded area spanning around a distal and medial external circumference; a grip area spanning around a proximal external circumference; and a cap or flip-cap to provide closure at a distal end to prevent evaporation of the flowable pharmaceutical composition.

The adapter as claimed above, being configured to connect to a cavity applicator on the distal end through a screw, slide, snap, or a combination of connecting mechanisms.

The adapter as claimed above, being configured to connect to a jar dispenser on the proximal end through a screw, slide, snap, or a combination of connecting mechanisms.

The adapter as claimed above, being configured to facilitate a transfer of cream and gel pharmaceutical preparations from larger dispensing jars into smaller containers.

The adapter as claimed above, being configured with a removable cap or flip-cap to retard evaporation a flowable semi-liquid pharmaceutical composition.

A metered dial-dispenser comprising: a cap to retard evaporation; a lid with a central outlet; a center screw; a piston; a body; and a rotatable base with a plurality of dial tabs spanning around its outer circumference.

The metered dial-dispenser as claimed above further including a dispenser lid configured to connect to a cavity applicator through a slide, snap, screw, or a combination of connecting mechanisms.

The metered dial-dispenser as claimed above further including a dispenser lid configured to mate with a removable adapter made of silicon, rubber, or other soft, elastomeric material to assist in application to sensitive body areas or cavities in humans and animals.

The metered dial-dispenser as claimed above wherein the removable cap being configured as a slide cap, snap cap, screw cap, or flip cap to retard evaporation and to facilitate connectivity.

The metered dial-dispenser as claimed above being configured for automated or manual loading from a larger container.

A non-metered cylindrical jar dispenser for dispensing or transferring flowable contents, the jar dispenser comprising: a removable cap to retard evaporation; a removable nozzle for dispensing contents including a flowable pharmaceutical composition; a removable lid with a central outlet to contain the contents; a barrel to house an inner chamber; and a removable piston for driving the contents.

The jar dispenser as claimed above configured to screw to an adapter.

The jar dispenser as claimed above, wherein the removable nozzle is configured for transferring flowable pharmaceutical composition.

The jar dispenser as claimed above being configured for automated or manual driving of the piston to dispense different volumetric dosages of flowable pharmaceutical composition through the central outlet and the removable nozzle.

The jar dispenser as claimed above configured with a threaded or unthreaded cap.

The jar dispenser as claimed above configured with a removable lid comprising a central outlet at its distal end that is externally threaded, a removable cap being configured as a screw-in cap to retard evaporation.

The jar dispenser as claimed above configured with a removable lid comprising a central outlet at its distal end that is externally unthreaded, a removable cap being configured as a slide-in cap to retard evaporation.

The jar dispenser as claimed above being configured to connect to a cavity applicator by means of an adapter.

The jar dispenser as claimed above configured to connect directly to a cavity applicator.

The jar dispenser as claimed above, the cavity applicator as claimed above, the metered dial-dispenser as claimed above, and the adapter as claimed above preferably made of an elastomeric or semi-elastomeric material.

A method of dispensing comprising: filling a dispenser jar with a flowable composition; securing a dispenser lid; screwing a nozzle to the dispenser lid; and pressing a piston of the dispenser jar to transfer the composition to other containers, cavities, or applicators.

The method as claimed above wherein the dispenser jar includes a piston at a proximal end, a barrel, a removable screw-on lid at a distal end with a central outlet, a nozzle, and a removable screw-on cap.

The method as claimed above, wherein the flowable composition is a flowable pharmaceutical composition of a type from the group consisting of: a gel, cream, lotion, and an ointment.

The method as claimed above further including pressing the piston with a manual or automated rod to transfer the flowable composition from the dispensing jar with accuracy and precision into smaller containers or cavity applicators.

The illustrations of embodiments described herein are intended to provide a general understanding of the structure of various embodiments, and they are not intended to serve as a complete description of all the elements and features of components and systems that might make use of the structures described herein. Many other embodiments will be apparent to those of ordinary skill in the art upon reviewing the description provided herein. Other embodiments may be utilized and derived, such that structural and logical substitutions and changes may be made without departing from the scope of this disclosure. The figures herein are merely representational and may not be drawn to scale. Certain proportions thereof may be exaggerated, while others may be minimized. Accordingly, the specification and drawings are to be regarded in an illustrative rather than a restrictive sense.

The description herein may include terms, such as "up", "down", "upper", "lower", "first", "second", etc. that are used for descriptive purposes only and are not to be construed as limiting. The elements, materials, geometries, dimensions, and sequence of operations may all be varied to suit particular applications. Parts of some embodiments may be included in, or substituted for, those of other embodiments. While the foregoing examples of dimensions and ranges are considered typical, the various embodiments are not limited to such dimensions or ranges.

The Abstract is provided to allow the reader to quickly ascertain the nature and gist of the technical disclosure. The Abstract is submitted with the understanding that it will not be used to interpret or limit the scope or meaning of the claims.

In the foregoing Detailed Description, various features are grouped together in a single embodiment for the purpose of streamlining the disclosure. This method of disclosure is not to be interpreted as reflecting an intention that the claimed embodiments have more features than are expressly recited in each claim. Thus, the following claims are hereby incorporated into the Detailed Description, with each claim standing on its own as a separate embodiment.

As described herein, example embodiments relate to an applicator for inserting flowable pharmaceutical preparations into a body cavity, an adapter for connecting a jar to a cavity dispenser, a jar dispenser with a nozzle for automated transferring and dispensing of flowable pharmaceutical compositions, and a metered dial-dispenser configured to connect to a cavity dispenser for humans and animals. Although the disclosed subject matter has been described with reference to several example embodiments, it may be understood that the words that have been used are words of description and illustration, rather than words of limitation. Changes may be made within the purview of the appended claims, as presently stated and as amended, without departing from the scope and spirit of the disclosed subject matter in all its aspects. Although the disclosed subject matter has been described with reference to particular means, materials, and embodiments, the disclosed subject matter is not intended to be limited to the particulars disclosed; rather, the subject matter extends to all functionally equivalent structures, methods, and uses such as are within the scope of the appended claims.

What is claimed is:

1. A cavity applicator comprising:
   a segmented plunger with circular dosing tabs on the segmented plunger and extruded sequential numbers on the segmented plunger in each inter-segment corresponding to a calibrated volumetric dosage, wherein a proximal end of the plunger contains a fused piston configured to be inserted through a distal end of a medication barrel;
   a medication barrel including a medication chamber configured for cream or gel flowable pharmaceutical compositions, the medication barrel configured to contain volumetric dosages ranging from half milliliter or less, to at least four milliliters of flowable compositions, the segmented plunger and fused piston configured to slide through inner walls of the medication barrel and push the flowable composition therein to exit through an outlet of the medication barrel when force is applied to the segmented plunger; and
   a removable cap to retard evaporation and prevent spillage of the contents inside the medication chamber of the cavity applicator.

2. The cavity applicator of claim 1, wherein the plunger preferably comprises eight visual and tactile dosing segments, each bounded by a dosing tab and calibrated to dispense a pre-determined fixed dosage of flowable pharmaceutical preparation.

3. The cavity applicator of claim 1, wherein each dosing inter-segment of the plunger houses an extruded or indented number that corresponds to a measurable and tactile dosage.

4. The cavity applicator of claim 1, wherein the plunger further comprises a piston and dome tip at the proximal end.

5. The cavity applicator of claim 1, wherein the plunger further comprises a digit trigger at a distal end.

6. The cavity applicator of claim 1, wherein the plunger and barrel can be combined to yield a segmented dosing interval.

7. The cavity applicator of claim 1, where each dosing tab and dosing inter-segment can be used for measuring and applying dosages via visual and tactile senses.

8. The cavity applicator of claim 1, wherein each dosing tab in the plunger translates to volumetric quantity of flowable composition dispensed from the applicator's proximal end by means of the interaction of the barrel and piston.

9. The cavity applicator of claim 1, wherein an external portion of the distal end of the barrel further comprises a dual usage extruded thumb grip area and cavity depth indicator, the thumb grip area providing a grip for holding the apparatus, the cavity depth indicator providing sensory depth information to the user when inserting the cavity applicator into a cavity.

10. The cavity applicator of claim 1, wherein the barrel being configured to house a one way ramp near a distal end to lock the plunger inside the barrel and to protect the contents from spillage at the distal end.

11. The cavity applicator of claim 1, wherein the barrel being configured to house a non-threaded area at a proximal end for connectivity.

12. The cavity applicator of claim 1, wherein the barrel being configured to house a threaded area at a proximal end for connectivity.

13. The cavity applicator of claim 1, wherein the barrel being configured to house an indented or extruded rim at an inner wall of a proximal end for connectivity.

14. The cavity applicator of claim 1, wherein the barrel being configured to house a plurality of calibrated extruded or indented circular dosing segments at an inner wall, each dosing segment being calibrated to encompass predetermined volumetric amounts of flowable composition.

15. The cavity applicator of claim 1, wherein the barrel being configured to house a plurality of calibrated extruded or indented circular dosing segments at an inner wall, each dosing segment being configured to interact with the plunger's piston to deliver a predetermined calibrated volumetric dosage while providing sensory feedback to an end user.

16. The cavity applicator of claim 1 wherein the removable cap is configured to screw, slide, or snap in and out to provide closure to the outlet at a proximal end of the barrel.

17. The cavity applicator of claim 1, wherein the medication chamber being configured to dispense solid cargo of a type from the group consisting of: pills, pellets, or lozenges.

18. The cavity applicator of claim 1 being configured for connection to a metered dial-dispenser on a proximal end by use of a screw, slide, snap, or a combination of connecting mechanisms.

* * * * *